United States Patent [19]

Swanson

[11] 4,198,712

[45] Apr. 22, 1980

[54] SCAPHOID IMPLANT

[76] Inventor: Alfred B. Swanson, 2945 Bonnell, SE., Grand Rapids, Mich. 49506

[21] Appl. No.: 21,624

[22] Filed: Mar. 19, 1979

Related U.S. Application Data

[63] Continuation-in-part of Ser. No. 951,317, Oct. 13, 1978, abandoned.

[51] Int. Cl.² ............................................. A61F 1/24
[52] U.S. Cl. ...................................... 3/1.91; 128/92 C
[58] Field of Search ................................ 3/1.9–1.91, 3/1; 128/92 C

[56] References Cited

U.S. PATENT DOCUMENTS

| | | | |
|---|---|---|---|
| 3,879,767 | 4/1975 | Stubstad | 3/1.91 |
| 3,924,276 | 12/1975 | Eaton | 3/1.91 |

OTHER PUBLICATIONS

"Silicone Rubber Implants for Replacement of Arthritic or Destroyed Joints in the Hand," by A. B. Swanson, Surgical Clinics of North America, vol. 48, No. 5, Oct. 1968, pp. 1113–1127.
Flexible Implant Resection Arthroplasty in the Hand and Extremities (Book) by Alfred B. Swanson, Published 1973, pp. 1–6, 15, 16, 30, 31 and 240–253.

Primary Examiner—Ronald L. Frinks
Attorney, Agent, or Firm—Price, Heneveld, Huizenga & Cooper

[57] ABSTRACT

A flexible implant for replacing the scaphoid bone of the wrist includes a one-piece body of resilient material. The body defines an inferior surface of slightly convex and oval shape with the apex of the surface lying in substantially a single plane and defining a trapezium articulate facet and a trapezoid articulate facet. A stabilizing stem extends outwardly from the inferior surface and generally perpendicular thereto. The body further defines a superior surface having a smooth, slightly convex shape and being adapted to articulate with the radius. An internal surface defined by the body has a lunate articular facet and a deep concavity, the latter adapted to articulate with the capitate. An external surface of generally smooth and convex shape is bounded by the inferior surface and the superior surface and defines a dorsal edge of the internal surface concavity. A posterior surface extends between the external surface and the proximal edge of the lunate articular facet. An anterior surface of generally triangular shape is bounded by the lunate facet, the deep concavity and the superior surface.

14 Claims, 14 Drawing Figures

SCAPHOID IMPLANT

CROSS REFERENCE TO RELATED APPLICATION

This application is a continuation-in-part of co-pending application Ser. No. 951,317, filed Oct. 13, 1978 now abandoned.

BACKGROUND OF THE INVENTION

The present invention relates to arthroplastic reconstruction of the human joints and more particularly to flexible implant resection arthroplasty of the wrist joint.

Silicone implants have been successfully employed in the restoration of function of the joints of the hand which have been affected by rheumatoid arthritis and similar pathological conditions. The procedures developed to employ the silicone implants have generally been found to be more successful than prior attempts to restore motion. Such prior attempts have included soft tissue arthroplasties and the use of metal implants. The prior conventional operational procedures to correct deformities of the wrist joint were not wholly satisfactory in producing proper function of the wrist joint which is necessary for proper function of the hand.

Aseptic necrosis and/or arthritis of the carpal bones is a frequent cause of disability of the wrist joint. Surgical treatment of conditions of the wrist joint have heretofore included intercarpal fusion, wrist fusion, local resection, proximal row carpectomy, bone grafting, radial styloidectomy, radial shortening or ulnar lengthening, and soft tissue interposition arthroplasty. Fusion procedures are not completely acceptable since the stability, power and mobility of the wrist are affected, although pain is relieved. Local resection procedures involving the removal of an irreversibly pathological bone, are complicated by migration of adjacent carpal bones into the space left after the resection. This migration results in instability in the wrist joint. Metallic and acrylic implants developed for replacement of carpal bones have not been totally satisfactory due to problems relating primarily to progression of the arthritic process, migration of the implant, breakdown of the implant material and absorption of bone due to hardness of the material inserted.

Due to these shortcomings of such prior operative procedures, intramedullary stemmed silicone rubber implants have been developed to replace the scaphoid bone and the lunate bone of the carpal row. These implants were designed to act as articulating spacers capable of maintaining the relationship of adjacent carpal bones after excision of the lunate or scaphoid bone while preserving mobility of the wrist. Examples of such prior carpal bone implants may be found in Applicant's work entitled "Flexible Implant Resection Arthroplasty On The Hand And Extremities", 1973 by the C. V. Mosby Company. Also, an example of an improved lunate implant may be found in Applicant's copending application, Ser. No. 900,188, entitled LUNATE IMPLANT, and filed Apr. 26, 1978.

Initial attempts to develop carpal implants resulted in the implants having essentially the same anatomical shape as the bones being replaced. The prior scaphoid implant was developed through exhaustive anatomical shaping and sizing of cadaver bones and roentgenographic studies of a variety of hands. The prior scaphoid implant was provided in progressive sizes for either the right or left hand due to mirror image differences in the bone structures. The concavities of the scaphoid implant were more pronounced than those found in the bone being replaced since such was felt necessary to increase stability of the implant. A stabilizing stem was formed integral with the implant and fitted into the trapezium. The intramedullary stem maintained the position of the implant postoperatively until the capsuloligamentous system healed around the implant.

As previously stated, the prior scaphoid implant was essentially an anatomical replica of the bone being replaced. Over ten thousand measurements were made on a random selection of one hundred and twenty specimens of scaphoid bones. Angles were measured with a goniometer and a series of convex and concave patterns were employed to size the curved surfaces of the bones. A mean value was established for each dimension and proportioned implant sizes were fabricated. The resulting implants included multi-faceted, angled and curvilinear surfaces. The concavity of the implant which articulated about the capitate bone was, however, deepened. It was then believed that an anatomically correct implant including such deeper concavitities resulted in more stable arthroplastic reconstruction.

SUMMARY OF THE INVENTION

In accordance with the present invention, a scaphoid implant is provided which results in increased stability over that heretofore obtained and which is not a multi-faceted, complexly surfaced implant mimicking the bone replaced. Essentially, the unique scaphoid implant includes an inferior surface of generally oval and convex shape, the apex of the surface lies in substantially a single plane. The surface defines a trapezium articulate facet and a trapezoid articulate facet. A stabilizing stem may extend outwardly and generally perpendicular to the inferior surface with the stem being adapted for insertion into the trapezium. The implant further includes a superior surface having a smooth, slightly convex shape in plan and defining a curvilinear palmar edge. The superior surface is adapted to articulate with the radius bone. An internal surface having a flat, planar lunate articulate facet and a deep concavity adjacent to this facet is also defined by the implant. The concavity is generally oval in plan and is adapted to articulate with the capitate bone. The implant further includes an external surface bounded by the inferior surface and the superior surface. The external surface defines a dorsal edge of the internal surface concavity is smooth and generally convex in shape. A posterior surface extends between the proximal edge of the external surface and the proximal edge of the lunate articulate facet. An anterior surface of generally triangular shape in plan includes a base coincident with the distal edge of the inferior surface. The anterior surface is bounded by the lateral edge of the concavity of the internal surface and by the palmar edge of the superior surface.

DETAILED DESCRIPTION OF THE PREFERRED EMBODIMENT

Figure 1:
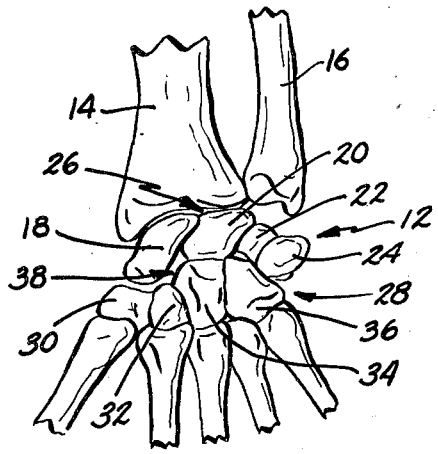
FIG. 1 is a fragmentary, anterior view of the wrist joint of a right hand showing the distal and proximal carpal rows.

With reference to the drawings, FIG. 1 illustrates an anterior view of the wrist joint of a right hand. The bones that make up the wrist joint include a proximal carpal row 12 adjacent to the radius 14 and the ulnar 16 of the arm. The proximal row 12 includes a scaphoid bone 18, a lunate bone 20, a triquetrum bone 22 and a pisiform bone 24. The joint 26 extending along the proximal carpal row of the wrist between the distal radius is referred to as the radiocarpal joint. The wrist joint further includes a distal carpal row 28. The distal carpal row includes a trapezium bone 30, a trapezoid bone 32, a capitate bone 34 and a hamate bone 36. The midcarpal joint 38 of the wrist extends between the distal and proximal carpal rows.

The configuration of each row of bones changes according to the position of the hand. Wrist movement is divided between the radiocarpal and midcarpal joints in a relatively complex manner and displacement of the bones is necessary for bone motion. Flexion and extension movements are fairly equally divided between the proximal and distal rows of the carpal bones while ulnar and radial deviation movements are mostly at the radiocarpal joint. Wrist disability results from anatomical distortion of the carpal bones or loss of integreity of their ligaments or secondary stiffness, all of which affects the joints.

The carpal bones are held together by short, interosseous ligaments. Ulnar collateral and radial collateral ligaments provide lateral support for the wrist. Palmar radiocarpal and dorsal radiocarpal ligaments maintain support of the carpal area. The fibers of the palmar radiocarpal ligament extend distally and obliquely from the radius, the triangular fibrocartilage and styloid process of the ulna. These ligaments define a symmetrical pattern due to insertions into the scaphoid, lunate, triquetrum and capitate bones. The integrity of the radiocarpal and ulnocarpal bands of ligaments should be maintained in any carpal bone surgery and these ligaments should not be interfered with or impinged on by the implant.

As seen in FIG. 1, the scaphoid bone 18 articulates proximally about the radius 14, distally about the trapezium 30 and trapezoid 32 and medially about the lunate 20 and capitate 34. The scaphoid bone includes a superior surface which is smooth, triangular, slightly convex and faces upwardly and outwardly and backwardly. The superior surface articulates with the triangular part of the inferior surface of the lower end of the radius. The inferior surface of the scaphoid bone faces downwardly, and backwardly and has the shape of a four-sided articulate facet which is broader behind than in front and is divided by a slight anteroposterior ridge into a larger external quadrilateral surface for articulation with the trapezium and a smaller, internal quadrilateral surface for articulation with the trapezoid. Both of these facets are slightly convex in all directions. The bone includes an external surface which faces backwards, upwards and downwards and is encroached upon by the superior and inferior surfaces. The external surface defines a rough groove to which ligaments are attached. The scaphoid internal surface defines a narrow rough space separating the superior from the external surface and for attaching an interosseous ligament, a slightly convex semi-lunar shaped articular facet which faces forwards and inwards to articulate with the lunate and a deep articular concavity which articulates with the outside of the head of the capitate. The scaphoid posterior surface is bounded by the semi-lunar shaped articular facet and defines a rough border for ligament attachment. The scaphoid anterior surface is generally triangular in shape, is rough and convex from side to side and concave from above and downwardly. The anterior surface is prolonged forwards at its base into a prominence for the attachment of the anterior annular ligament and the abductor policis muscle. This surface is called the tuberosity of the scaphoid.

As set forth above, initial attempts to develop a scaphoid implant involved the detailed and critical study of approximately one hundred and twenty scaphoid bones. This study resulted in a series of graduated implants which were anatomically very similar to and mimicked the bone replaced. These prior implants were successfully employed in arthroplastic reconstruction of the wrist joint. However, the stability obtained did not as closely approach that normally present in a non-defective wrist joint as was desired.

Figure 2:
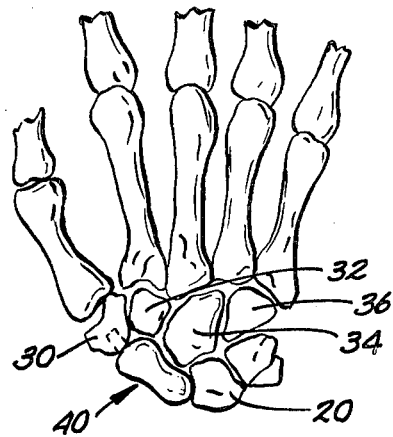
FIG. 2 is a posterior view of the wrist joint of a right hand including a scaphoid implant in accordance with the present invention.

As seen in FIG. 2, and as explained in detail below, the present invention provides a scaphoid implant generally designated 40. The implant 40 is surgically positioned to articulate with the trapezium 30, the trapezoid 32, the capitate 34, the lunate 20 and the radius 14.

Figure 3:
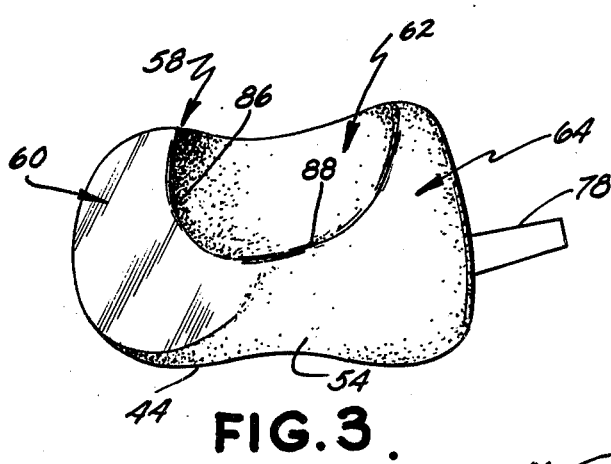
FIG. 3 is a perspective view showing the internal surface of the implant.
Figure 4:
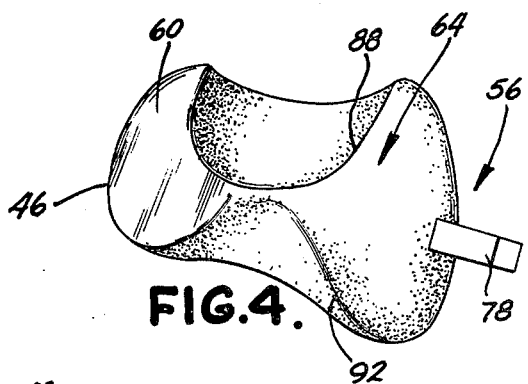
FIG. 4 is another perspective view showing the internal surface and the inferior surface of the implant.
Figure 5:
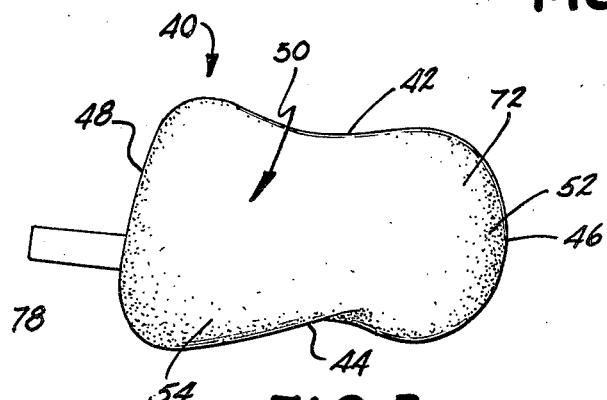
FIG. 5 is a plan view illustrating the superior and posterior surfaces of the implant.

As seen in FIG. 5, the implant 40 includes a dorsal edge 42, a palmar edge 44, a proximal edge 46 and a distal edge 48. The body defines an external surface 50, a posterior surface 52 and a superior surface 54. Also, as seen in FIGS. 3, 4 and 6, the body further defines an inferior surface 56, an internal surface 58 having a lunate articulate facet 60 and a deep concavity 62, and an anterior surface 64.

Figure 7:
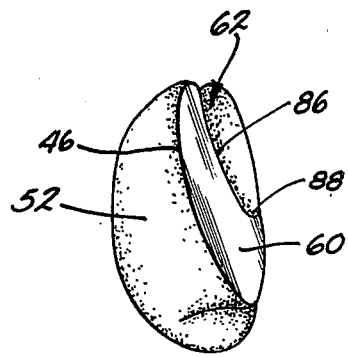
FIG. 7 is a rear, perspective view showing the posterior surface and a portion of the internal surface of the implant.
Figure 8:
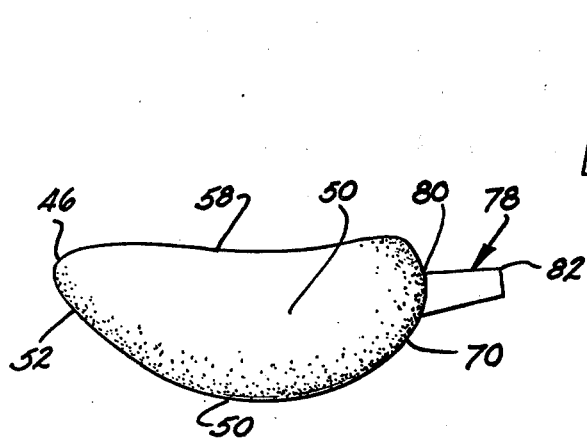
FIG. 8 is an elevational view showing the superior surface of the implant.
Figure 9:
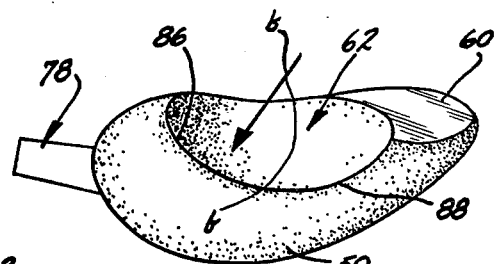
FIG. 9 is a perspective view showing the interface between the internal surface and the superior surface of the implant along the dorsal edge thereof.
Figure 10:
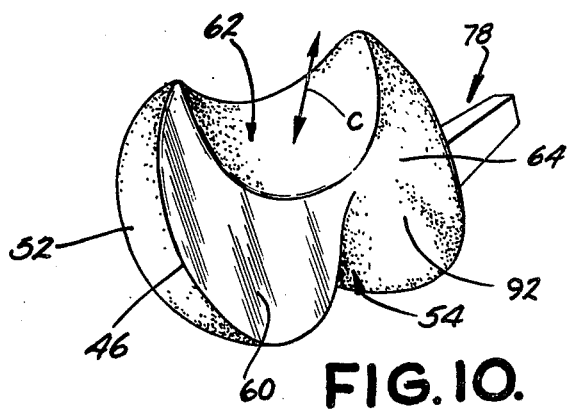
FIG. 10 is a perspective view showing the internal surface and the anterior surface of the implant.

As seen in FIGS. 5, 7 and 8, the external surface 50 is generally smooth and convex in shape as it extends from dorsal edge 70 of the inferior surface 56 to a point where it joins to the posterior surface along a transition area 72. The interface between the external surface and the posterior surface is not well defined by the body but is defined more in terms of anatomical positioning when the implant is in situ. The external surface 50 is also convex along its transverse direction from the dorsal edge 42 to the palmar edge 44 of the body. The external surface 50 smoothly joins into the superior surface 54. The dorsal edge of the external surface 50 is coincident with the dorsal edge of the internal surface 58 and the dorsal edge 42 of the body and defines a boundary line or edge of the concavity 62.

Figure 6:
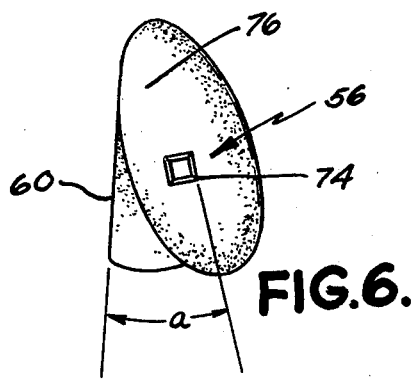
FIG. 6 is an elevational view showing the inferior surface of the implant.

The inferior surface 56, as best seen in FIGS. 3, 4, 6 and 8, is generally oval in shape in plan (FIG. 6). The surface is bounded by the external surface 50 and by the anterior surface 64. The surface is generally convex from the external surface 50 to the anterior surface 64 and the apex of the surface lies in substantially a single plane. The surface defines a trapezium articulate facet 74 and a trapezoid articulate facet 76. Extending outwardly from and generally perpendicular to the surface 56 is a stabilizing stem 78. The stem 78 is tapered from its base 80 where it joins the surface 56 to its free end 82. Further, as seen in FIG. 6, the stem is generally rectangular in cross section. The stem 78 is adapted to be inserted into the trapezium bone and stabilizes the implant postoperatively. The trapezium bone is preferably selected as a point for insertion of the stabilizing stem since the relative motion between the implant and the carpal bones is at a minimum with the trapezium. The centerline of the apex of the inferior surface 56 is angled at an angle a with respect to the plane of the lunate articulate facet 60.

As seen in FIGS. 3, 7, 9 and 10, the internal surface 58 includes the lunate articular facet 60 and the deep concavity 62. The facet 60 is planar or flat and lies in a single plane. Further, the facet is generally semi-lunar in shape in plan with a distal edge 86 thereof defining a portion of the medial edge of the concavity 62. The proximal edge of the facet 60 is coincident with the proximal edge 46 of the body 40 and hence with the proximal edge of the posterior surface 52. The surface 60 is flat as opposed to the slightly convex or curved surface presented by the scaphoid bone which the implant replaces and is also flat as opposed to the curved surface presented by the prior art scaphoid implant discussed above. This surface abuts against and articulates with the lunate bone 20 as seen in FIG. 2. Unexpectedly, the flattening of the surface 60 so that it does not mimic the scaphoid bone replaced increases the stability of the implant. The concavity 62 is cupped in shape, having a longitudinal radius b and transverse radius c. This concavity is adapted to articulate with and receive the head of the capitate bone 34. The concavity 62 is deeper than that found in the scaphoid bone which the implant replaces. The deep concavity 62 includes a curvilinear medial edge 88 which lies in substantially the same plane as a lunate articulate facet 60. The plane of the lunate articulate facet, as seen in FIG. 8, is substantially perpendicular to the inferior surface 56 single plane. This deepening of the concavity increases the stability of the implant in situ. The concavity opens through and its anterior edge 88 lies in the same plane as the plane of the lunate facet 60.

The superior surface 54 of the implant is best seen in FIGS. 3, 4 and 5. This surface is smoothly convex in shape as it extends from the internal surface 58 and the anterior surface 64 to the external surface 50. The apex of the concavity of the surface 54 as it extends from the distal edge 48 to the proximal edge 46 of the implant is, however, curvilinear and slightly concave in form. The transverse width of the implant 40 at the proximal edge 46 is less than the transverse or overall width of the implant at its distal edge 48. The surface 54 is adapted to articulate about the inferior end of the radius.

The anterior surface 64 of the implant is generally triangular in shape in plan with the base thereof coincident with the lower or proximal edge of the inferior surface 56. One of the side edges of the anterior surface 64 is defined by the internal edge 88 of the concavity 62. The opposite side edge 92 of the anterior surface 64 is coincident with a portion of the palmar edge of the superior surface 54. The anterior surface 64 is slightly convex in shape and is smooth between its boundaries.

Figure 12:
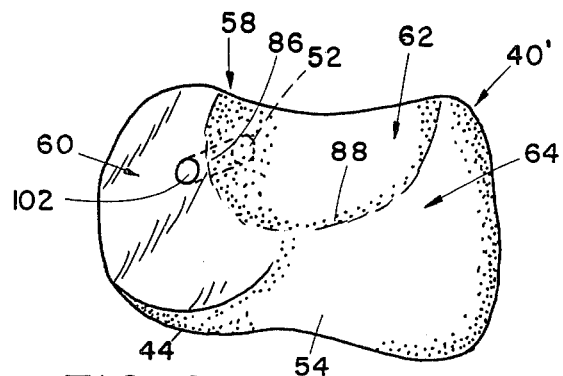
FIG. 12 is a perspective view showing the internal surface of an alternative embodiment of the present invention.

An alternative embodiment of implant is illustrated in FIG. 12. and designated 40'. Implant 40' differs from the above described implant in that the body thereof defines an aperture or bore 102 extending from the lunate articulate facet to the posterior surface 52. The bore 102 opens through these surfaces. As explained in detail below, the bore is provided to fix or inhibit dislocation of the implant through the use of a segment of the extensor carpi radialis brevis (ECRB) tendon.

It is believed that when the implant is fixed with the tendon segment, the stabilizing stem 78 may be eliminated. For this reason, the implant 40' is illustrated without a stabilizing stem.

In a presently existing embodiment of the scaphoid implant 40, the overall longitudinal dimension of the body from the proximal edge to the distal edge at the inferior face 56 is approximately 1.05 inches. The overall width of the body along the proximal edge 46 is approximately 0.579 inches. The overall width of the body at the distal edge is approximately 0.675 inches. The body therefore has a slight taper of approximately 2°. The stabilizing stem 78 has a square base 80 with a side dimension of approximately 0.138 inches and a square free end 82 with a side dimension of approximately 0.100 inches. The overall longitudinal dimension of the stabilizing stem 78 is approximately 0.270 inches. The implant has an overall thickness measured in a dorsal edge view from the internal surface 58 to the apex of the external surface 50 of 0.480 inches. The stabilizing stem 78 is offset from the longitudinal centerline of the body 40 and the dorsal edge thereof is approximately 0.315 inches from the dorsal edge 42 of the body. The longitudinal centerline of the apex of the inferior surface 56 is angled with respect to the plane of the lunate facet 60 at an angle a of about 20°. Radius b is approximately 0.812 inches and radius c is approximately 0.68 inches.

It is preferred that the implant be fabricated in proportionally increased sizes in order to provide a proper fit for the individual patient. Also, due to the mirror image differences between the right and left wrist, right and left mirror image implants must be provided. As the implant is increased in size, the angular relationship between the long axis or the longitudinal centerline of the inferior surface to the lunate facet (angle a) also increases. Angle a increases in the range of 20° to 40°. The ratio of overall height of the implant to the overall length thereof from its proximal edge to its distal edge will vary within the approximate range of 0.45 to 0.51. The ratio of the length or width dimension of the proximal edge of the body to the length or width dimension of the distal edge of the body will vary within the approximate range of 0.84 to 0.90. Finally, the degree of taper of the body from the proximal to the distal edge may vary within the range of 1° to 2°. Basically, however, the larger sized implants result from proportional size increases.

The implant in accordance with the present invention results in an improved fit and is firmly supported on all sides by adjacent bones. The implant is analogous to a ball bearing in function and must be surrounded by a "housing". Therefore, a tight capsuloligamentous structure should be insured. The ligamentous structure should be repaired to prevent instability. The stem 78 is provided primarily to stabilize the implant during the early postoperative phase.

Insertion of the scaphoid implant is indicated for avascular necrosis or in the case of a longstanding dislocation. The implant should not be employed when the arthritic involvement is not localized to the scaphoid articulations, if complete relief of pain is sought. Loss of integrity of the capsular structures due to fracture dislocation or collapsed deformity of the wrist may be a contra-indication to the particular implant procedure unless the carpal bone relationship is reestablished and ligaments are repaired.

A surgical procedure for implantation of the scaphoid implant involves either a volar or a dorsolateral incision. The superficial sensory branches of the radial nerve should be meticulously preserved. Dissection is carried down between the first and second extensor compartments and the radial artery. The tendon of the extensor policis longus is retracted ulnarly and the incision is carried downward radially to the extensor capri radialis longus tendon. A distally based capsular flap is preserved as it is dissected close to the radius and the underlying scaphoid bone. The bone may be removed piecemeal with a rongeur. Care should be taken to avoid the underlying palmar ligaments. The correct size of the implant is determined by using a test set of implants. The implant of a size which will comfortably fit into the space left by the excision of the scaphoid is selected. A hole is formed with a drill or curette in the trapezium to accept the stem of the implant. The hole should be directed down the middle of the bone and at such an angle that the implant will be anatomically oriented. When a satisfactory fit has been obtained, and with an implant in position, the wrist joint is moved passively in all directions to verify stability. Before the implant is finally inserted, the anterior capsuloligamentous structures should be inspected. If they are loose, they should be reinforced with Dacron sutures and, if torn, they must be repaired. A slip of flexor capri radialis or a part of the radiocapitate ligament may be used to reinforce this area. Temporary fixation may be employed to stabilize the position of the implant during the early healing process. For example, Kirschner wire or a suture may be placed through the body of the implant into the radius or adjacent carpal bone.

Figure 11:
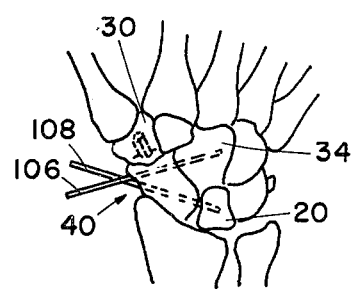
FIG. 11 is a posterior view of the wrist joint of the right hand showing the scaphoid implant temporarily transfixed with a Kirschner wire.

An example of temporary fixation with Kirschner wire is illustrated in FIG. 11. As shown therein, two lengths of wire 106, 108 are passed through the implant 40. Length 106 is passed into the adjacent capitate bone 34. Length 108 is passed through the implant and into the adjacent lunate bone 20. The wires should be passed as a separate stab entry rather than through the previously made incision. Care should be taken to avoid the superficial radial nerve branches by direct observation through the incision. Care in positioning the wires will avoid tenting of the skin thereabout which would provide a possible entry point for infection. Kirschner wire fixation into the adjacent capitate and lunate should not allow implant subluxation with tested motion. It is preferred that a window in the cast be formed to prevent wobbling of the cast on the wire. Further, it is preferred that a long arm cast be employed to prevent "positioning" of the arm and resultant movement across the exposed Kirschner wire.

The dorsal capsule is then tightly sutured and repaired over the implant by means of an inverted knot technique. The wound is then closed in layers and a scaphoid type short cast applied. The extremity should be elevated for three to four days.

Figure 13:
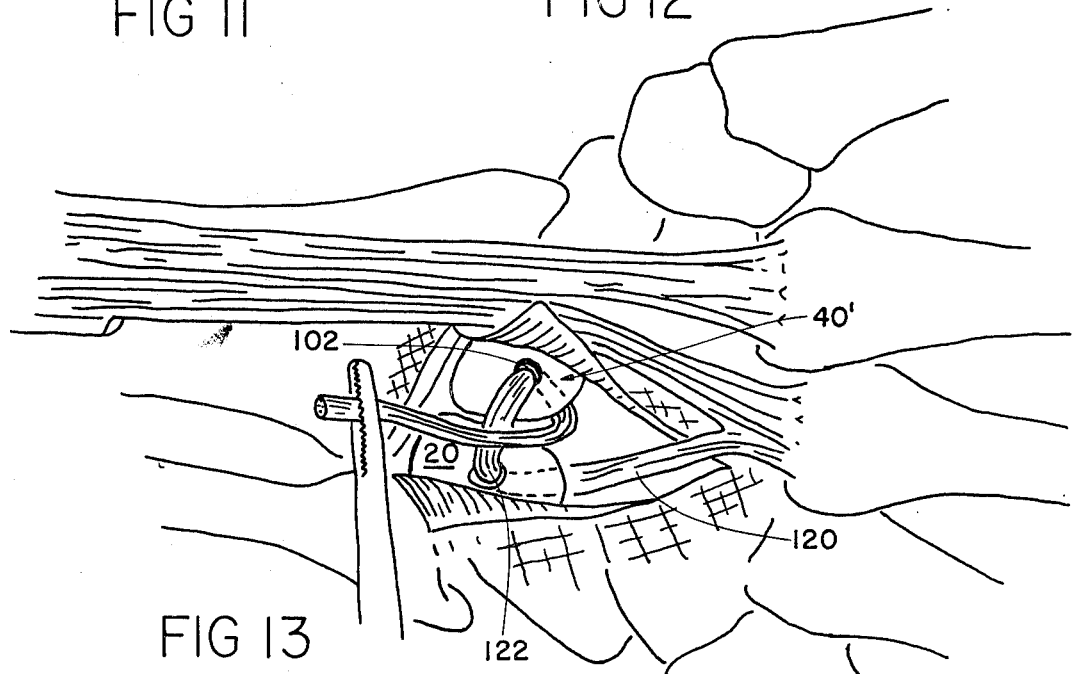
FIGS. 13 and 14 illustrate a surgical procedure for reconstruction of the scapho-lunate ligament to fix the implant.
Figure 14:
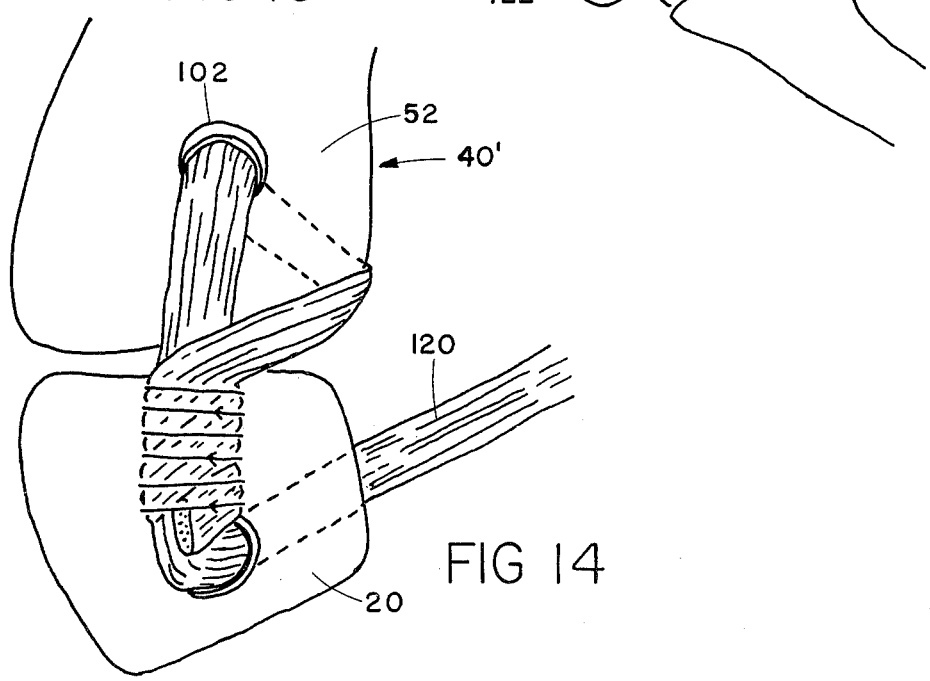

In cases associated with rotary subluxation of the scaphoid, scapho-lunate diastasis, capitate shift and other instabilities of the wrist joint, special consideration should be given for stabilization of the implant and reconstruction of the capsular and intercarpal ligamentous structures. When such reconstruction is anticipated, the alternative embodiment of the implant illustrated in FIG. 12 is employed. As seen in FIGS. 13 and 14, the reconstruction of the scapho-lunate ligament is accomplished with a distally based ⅛ diameter, 8–9 cm. slip 120 of the ECRB tendon. When employing this procedure, a 3 mm. hole or bore 122 is formed through the lunate bone 20. A plug cutter is employed to core the hole 102 in the scaphoid. It is preferred that the hole size be approximately 3 mm. in diameter and 6 to 8 mm. from the edge of the scaphoid implant. The ECRB tendon slip is passed through the lunate bone 20 with a wire loop pull-through technique. The tendon slip 120 is then passed over the posterior surface 52 of the implant body, through the bore 102 and back around the implant, as shown. The tendon slip is then securely fixed to itself with multiple 3–0 Dacron sutures. When employing this technique, temporary stabilization of the scaphoid implant, as illustrated in FIG. 11, for a 3 to 4 week period should also be employed. The joint is immobilized for 8 weeks in a long arm thumb spica cast. As set forth above, it is believed that when the implant is formed with the bore 102 that the stabilizing stem 78 may be eliminated. The tendon slip may sufficiently stabilize the structure to inhibit dislocation.

The scaphoid implant in accordance with the present invention is easily and relatively inexpensively manufactured through conventional molding techniques from medical grade silicone elastomers. The implant is surgically positioned through relatively simple surgical procedures and has a potential of permitting wrist motion with increased stability from that heretofore obtained, mobility and freedom from pain. The above description should be considered as that of the preferred embodiment. The true spirit and scope of the present invention may be determined by reference to the appended claims.

The embodiments of the invention in which an exclusive property or privilege is claimed are defined as follows:

1. An implant for replacement of the scaphoid bone and insertable surgically adjacent the trapezium, the trapezoid, the lunate, the capitate and the radius, said implant comprising:
   a one-piece body of resilient material, said body defining:
   an inferior surface of generally oval shape in plan and being slightly convex, the apex of said surface lying in substantially a single plane and defining a trapezium articulation and a trapezoid articulation;
   a superior surface having a smooth slightly convex shape in plan and defining a curvilinear palmar edge, said superior surface adapted to articulate with the radius;

an internal surface having a flat lunate articulate facet and a deep concavity adjacent to said facet, said concavity being generally oval in plan and adapted to articulate with the capitate;

an external surface bounded by said inferior surface and said superior surface and defining a dorsal edge of said internal surface concavity, said external surface being smooth and generally convex in plan;

a posterior surface extending between said external surface and a proximal edge of said lunate articulate facet, said proximal edge being generally semicircular in shape; and an anterior surface of generally triangular shape in plan including a base coincident with a proximal edge of said inferior surface and bounded by said lunate facet, said deep concavity and said superior surface.

2. An implant as defined by claim 1 wherein said body defines a bore therethrough usable to fix the implant with a tendon slip.

3. An implant as defined by claim 1 wherein the proximal edge of said posterior surface lies in the same plane as the lunate articular facet and said anterior surface is convex between said deep concavity and said superior surface.

4. An implant as defined by claim 1 wherein said deep concavity includes a curvilinear medial edge lying in substantially the same plane as said lunate articular facet.

5. An implant as defined by claim 3 wherein said inferior surface single plane is substantially perpendicular to the plane of said lunate articular facet.

6. An implant as defined by claim 4 wherein the centerline of the inferior surface is angled upwardly at an angle a with respect to the plane of the internal surface lunate articular facet.

7. An implant as defined by claim 6 wherein said centerline of said inferior surface is angled upwardly at an angle within the range of 20° to 40°.

8. An implant as defined by claim 6 wherein said body has a ratio of overall height to overall length from its proximal edge to its distal edge within the approximate range of 0.45 to 0.51.

9. An implant as defined by claim 7 wherein the ratio of the length of the proximal edge of said body to the distal edge of said body is within the approximate range of 0.84 to 0.90.

10. An implant as defined by claim 8 wherein said body has an included angle from the proximal edge thereof to the distal edge thereof within the approximate range of 1° to 2°.

11. An implant as defined by claim 1 wherein said body further includes a stabilizing stem extending outwardly and generally perpendicular to said inferior surface, said stem adapted for insertion into the trapezium.

12. An implant as defined by claim 2 wherein said body further includes a stabilizing stem extending outwardly and generally perpendicular to said inferior surface, said stem adapted for insertion into the trapezium.

13. An implant as defined by claim 9 wherein said body defines a bore therethrough usable to fix the implant with a tendon slip.

14. An implant as defined by claim 13 wherein said body further includes a stabilizing stem extending outwardly and generally perpendicular to said inferior surface, said stem adapted for insertion into the trapezium.

* * * * *

UNITED STATES PATENT AND TRADEMARK OFFICE
CERTIFICATE OF CORRECTION

PATENT NO. : 4,198,712
DATED : April 22, 1980
INVENTOR(S) : Alfred B. Swanson

It is certified that error appears in the above-identified patent and that said Letters Patent are hereby corrected as shown below:

Column 2, line 22:

"concavitities" should be --concavities--;

Column 2, line 49:

After "concavity" insert --and--;

Column 7, line 46:

After "of" insert --available--;

Column 8, lines 1-2:

"positioning" should be --"pistoning"--.

Signed and Sealed this

Twenty-second Day of July 1980

[SEAL]

Attest:

SIDNEY A. DIAMOND

Attesting Officer    Commissioner of Patents and Trademarks